United States Patent
Florent et al.

(10) Patent No.: US 9,904,978 B2
(45) Date of Patent: Feb. 27, 2018

(54) PAIRING OF AN ANATOMY REPRESENTATION WITH LIVE IMAGES

(71) Applicant: KONINKLIJKE PHILIPS N.V., Eindhoven (NL)

(72) Inventors: Raoul Florent, Ville d'Avray (FR); Olivier Pierre Nempont, Suresnes (FR); Pascal Yves Francois Cathier, Asnieres-sur-Seine (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 898 days.

(21) Appl. No.: 14/359,112

(22) PCT Filed: Nov. 8, 2012

(86) PCT No.: PCT/IB2012/056252
§ 371 (c)(1),
(2) Date: May 19, 2014

(87) PCT Pub. No.: WO2013/072818
PCT Pub. Date: May 23, 2013

(65) Prior Publication Data
US 2014/0294152 A1    Oct. 2, 2014

(30) Foreign Application Priority Data
Nov. 18, 2011 (EP) .................................... 11189646

(51) Int. Cl.
*G06T 3/00* (2006.01)
*G06T 7/00* (2017.01)
(Continued)

(52) U.S. Cl.
CPC ............ *G06T 3/0068* (2013.01); *A61B 6/487* (2013.01); *A61B 6/5235* (2013.01);
(Continued)

(58) Field of Classification Search
CPC ..... A61B 6/4441; A61B 6/4464; A61B 6/487; A61B 6/503; A61B 6/5235;
(Continued)

(56) References Cited

U.S. PATENT DOCUMENTS

| 5,274,551 A | 12/1993 | Corby, Jr. |
| 2007/0167721 A1 | 7/2007 | Pfister et al. |

(Continued)

FOREIGN PATENT DOCUMENTS

| WO | WO2010067300 | 6/2010 |
| WO | WO2011039681 | 4/2011 |

OTHER PUBLICATIONS

Karar et al., "Model-updated Image Guided Minimally Invasive Off-Pump Transcatheter Aortic Valve Implantation", presented Sep. 22, 2011, MICCAI 2011, Part I, LNCS 6891, pp. 275-282.*

(Continued)

*Primary Examiner* — Glen Kao

(57) ABSTRACT

The present invention relates to pairing an anatomy representation with live images. In order to provide an enhanced and more flexible pairing of an anatomy representation with live images, for pairing an anatomy representation with live images, reference projected-anatomy image data of a device in a spatial relation to the anatomy is provided (100), wherein the image data comprises at least a first and second image showing the device from different viewing angles. Further, an anatomy representation with an anatomy frame of reference is provided (200). The anatomy representation is brought (300) into spatial coherence with the at least first and second image of the reference projected anatomy image data. A three-dimensional model of the device within the anatomy frame of reference is computed (400) from the projected anatomy image data. At least one live image is provided (500) containing the device. The model and the at least one live image are registered (600) based on the device (Continued)

information contained in the live image. The anatomy representation is brought (700) into spatial correspondence with the at least one live image based on the registering of the model and the at least one live image. The registered anatomy is combined (800) with the at least one live image.

11 Claims, 5 Drawing Sheets

(51) Int. Cl.
*A61B 6/00* (2006.01)
*G06T 7/33* (2017.01)

(52) U.S. Cl.
CPC ............ *G06T 7/0012* (2013.01); *G06T 7/337* (2017.01); *A61B 6/4441* (2013.01); *A61B 6/4464* (2013.01); *A61B 6/503* (2013.01); *G06T 2207/10016* (2013.01); *G06T 2207/10121* (2013.01); *G06T 2207/30048* (2013.01); *G06T 2207/30101* (2013.01); *G06T 2210/41* (2013.01)

(58) Field of Classification Search
CPC . G06T 2207/10016; G06T 2207/10121; G06T 2207/30048; G06T 2207/30101; G06T 2210/41; G06T 3/0068; G06T 7/0012; G06T 7/003
See application file for complete search history.

(56) References Cited

U.S. PATENT DOCUMENTS

| | | |
|---|---|---|
| 2008/0247621 A1 | 10/2008 | Zarkh et al. |
| 2009/0022381 A1 | 1/2009 | Gorges |
| 2009/0281418 A1 | 11/2009 | Ruijters |
| 2010/0145193 A1 | 6/2010 | Florent et al. |
| 2011/0164035 A1* | 7/2011 | Liao ................... G06T 7/0024 345/419 |
| 2011/0222750 A1 | 9/2011 | Liao |
| 2013/0011030 A1* | 1/2013 | Tzoumas ................ G06T 7/74 382/128 |
| 2013/0279825 A1* | 10/2013 | Liao ..................... G06T 11/60 382/284 |

OTHER PUBLICATIONS

Kempfert et al., "Dyna-CT During Minimally Invasive Off-Pump Transapical Aortic Valve Implantation", 2009, Annals of Thoracic Surgery, vol. 88, p. 2041.*

John et al., "System to Guide Transcatheter Aortic Valve Implants Based on Interventional C-arm CT Imaging", Presented no later than Sep. 24, 2010, MICCAI 2010, Part I, LNCS 6361, pp. 375-382.*

* cited by examiner

PAIRING OF AN ANATOMY REPRESENTATION WITH LIVE IMAGES

CROSS-REFERENCE TO PRIOR APPLICATIONS

This application is the U.S. National Phase application under 35 U.S.C. § 371 of International Application Ser. No. PCT/IB2012/056252, filed on Nov. 8, 2012, which claims the benefit of European Application Ser. No. 11189646.0, filed on Nov. 18, 2011. These applications are hereby incorporated by reference herein.

FIELD OF THE INVENTION

The present invention relates to an apparatus for pairing an anatomy representation with live images, a corresponding method for pairing an anatomy representation with live images, a computer program element, a computer readable medium, and a method for operating a device.

BACKGROUND OF THE INVENTION

X-ray imaging systems are used in operating room environments. For example, Trans-catheter Aortic Valve Implantation (TAVI) is a very important operation where the registration of an anatomy representation derived from pre- or peri-interventional data with live images is very challenging. For example, WO 2010/067300 A1 relates to automatic road-mapping for heart valve replacement comprising acquiring an X-ray image of a vessel root region of the heart with injected contrast agent and acquiring a current fluoroscopy image of the vessel root region with a replacement valve inserted into the vessel. A calculation unit identifies vessel information data within the acquired image and models a vessel root representation using the vessel information data. A composite image is generated by a combination of the vessel root representation with the at least one fluoroscopy image.

SUMMARY OF THE INVENTION

There may be a need to provide an enhanced and more flexible pairing of an anatomy representation with live images.

The object of the present invention is solved by the subject-matter of the independent claims, wherein further embodiments are incorporated in the dependent claims.

It should be noted that the following described aspects of the invention apply also for the apparatus, the method for pairing an anatomy representation with live images, the computer program element, the computer readable medium, and the method for operating a device.

According to a first aspect of the present invention, an apparatus for pairing an anatomy representation with live images is provided, comprising an interface unit and a processing unit. The interface unit is configured to provide reference projected-anatomy image data of a device in a spatial relation to an anatomy. The image data comprises at least a first and second image showing the device from different viewing angles. The interface unit is also configured to provide at least one live image containing the device. The processing unit is configured to provide a representation of the anatomy with an anatomy frame of reference, and to bring the anatomy representation into spatial coherence with the at least first and second image of the reference projected anatomy image data. The processing unit is also configured to compute a three-dimensional model of the device within the anatomy frame of reference from the projected anatomy image data, and to register the model and the at least one live image based on the device information contained in the live image. The processing unit is also configured to bring the anatomy representation into spatial correspondence with the at least one live image based on the registering of the model and the at least one live image, and to combine the registered anatomy with the at least one live image.

According to a further exemplary embodiment, the apparatus comprises a display unit, configured to visualize a live image overlaid with the anatomy representation.

According to a second aspect of the present invention, an X-ray imaging system is provided, comprising an X-ray source, an X-ray detector, and an apparatus as described above. The X-ray source is configured to radiate X-ray radiation towards the detector radiating at least a part of a region of interest of an object. The X-ray detector is configured to provide the reference projected-anatomy image data of the device, and to provide the at least one live image.

According to a third aspect of the present invention, a method for pairing an anatomy representation with live images is provided, comprising the steps of:

a) providing reference projected-anatomy image data of a device in a spatial relation to the anatomy, the image data comprising at least a first and second image showing the device from different viewing angles;
b) providing an anatomy representation with an anatomy frame of reference;
c) bringing the anatomy representation into spatial coherence with the at least first and second image of the reference projected anatomy image data;
d) computing a three-dimensional model of the device within the anatomy frame of reference from the projected anatomy image data;
e) providing at least one live image containing the device;
f) registering the model and the at least one live image based on the device information contained in the live image;
g) bringing the anatomy representation into spatial correspondence with the at least one live image based on the registering of the model and the at least one live image; and
h) combining the registered anatomy with the at least one live image.

With respect to the order of the steps it is noted that step a) is performed before step e). The data for step b) may have been computed or otherwise prepared beforehand. For step c), steps a) and b) must have been performed. Step d) is performed after step c), but can be performed before or after step e). For step f), steps d) and e) must have been performed already. Step h) requires step g) to be performed. Step g) is based on step f).

According to a further exemplary embodiment, the at least one live image has any viewing angle.

For example, the viewing angle of the at least one live image is different from the viewing angle of the least first and second image of the reference projected image data.

According to a further exemplary embodiment, the reference projected-anatomy image data are obtained using a contrast agent and the at least one live image is obtained without use of a contrast agent.

According to a further exemplary embodiment, the above-described method is used for assistance during Trans-catheter Aortic Valve Implantation (TAVI).

According to a further example, the spatial relation is be achieved by a locking of the device in the anatomy, i.e. a state where movement of the device with respect to the considered anatomy part is at least very minimal, if not suppressed completely. However, this anatomy part can itself be in motion with respect to the patient body. For example, an enforcement protocol is provided, which is enforcing the locking of the device in a location that is spatially connected to the target anatomy both at aortagram and live time images.

According to a further exemplary embodiment, the device is a pigtail catheter or a part thereof, which can be locked into the aortic root, for instance in one of the aortic valve's cups.

According to a further exemplary embodiment, the anatomy is subjected to a (natural) regular motion within its frame of reference, which motion can be decomposed in several repetitive motion phases. The above described method further comprises the following: In step a), the reference projected image data are a sequence of reference projected image data along time, containing the anatomy during its several motion phases. In step d), a sequence of three-dimensional models of the device along time is computed. In step e), a sequence of live images along time is provided. The method further comprises a step i) of selecting at least one three-dimensional model along time and at least one live image along time corresponding to a same motion phase. In step f), registration is performed between the at least one selected three-dimensional model and at least one live image corresponding to the same motion phase.

For example, the motion can be heart beating, but also breathing, etc. The invention can thus be used, for example, in abdominal interventions, e.g. abdominal aortic aneurysm endo-treatment, where mainly breathing is the motion cause, and, of course, for cardiac purposes.

According to a fourth aspect of the present invention, a computer program element is provided, which, when being executed by a processing unit is adapted to carry out the method described above.

According to a fifth aspect of the present invention, a computer readable medium having stored thereon a program element is provided, which, when being executed by a processing unit is adapted to carry out the method described above.

According to a sixth aspect of the present invention, a method for operating a device comprises the following steps: a) pairing an anatomy representation with live images according to the method described above, and b) visualizing a live image overlaid with the anatomy representation.

The anatomy representation can contain tagged anatomy details plus measurements, e.g. the valve cups, the coronary ostia etc. The various valve measurements can be part of this representation and can therefore be overlaid on the live image.

According to an aspect of the invention the overlaying of an anatomy representation with live images is provided, based on acquiring at least a pair of 2D images under different viewing angles as reference images, and featuring i) the footprint of a 3D anatomy representation seen in projection and ii) the projection of a device placed in spatial relation with an anatomy referential. The overlaying is further based on co-registering the 3D anatomy representation with the several reference images. From this co-registration result and from the footprints of the device observed in the projected anatomy images, a 3D model of the device is computed within the 3D anatomy representation. The overlaying is further based on acquiring at least one 2D live image, and on registering the 3D device model. Therefore, the registration of the attached anatomy representation to this 2D live image is based on the device information both from the 3D device model and from the live device footprint. The overlaying is further based on using the result of this registration to correctly overlay or superimpose a projection of the anatomy representation onto the live image or vice versa.

According still to a further aspect of the invention, the accurate registration of a 3D anatomy representation with a 2D live view is provided by computing a 3D model of a device located in correspondence of an anatomy based on several projection images featuring both the device and the anatomy footprints. This 3D model is used to register the anatomy with a live image featuring the device.

According to an aspect of the present invention, a device locking in the anatomy referential, i.e. the device is locked, is combined with the several-view-based device modeling technology. A method is proposed for the accurate registration of a 3D anatomy representation with a 2D live view, where the anatomy is invisible and where the 2D viewing angle is varying.

In other words, according to an aspect of the present invention it is proposed a method where one computes a 3D model of a device locked into an anatomy, which computing is based on several projection images featuring both the device and the anatomy footprints, and where this model is used to register the anatomy with a live image featuring the device (but not the anatomy) and acquired under any viewing angle.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

In the following, the invention is exemplarily described as being used in the context of an X-ray imaging system for Trans-catheter Aortic Valve Implantation (TAVI). But the invention can also be used in the context of the replacement of other types of heart valves, such as pulmonary, mitral and tricuspid valves or in the context of other medical operations, such as vascular endo-procedures, for instance the endo-treatment of Abdominal Aortic Aneurysms. In TAVI interventions, a critical point is the precise positioning of the implantable device under fluoroscopy prior to deployment. To achieve this positioning, a supra-aortic angiography (with contrast agent) can be performed in order to determine the optimal projection of valve deployment. A picture or image, featuring good contrast, can be selected, stored, and subsequently used as a pre-implant reference image. The contrast injection can be achieved through a so-called pigtailed catheter placed in the aortic root. In order to facilitate accurate positioning, road-mapping or outlining methods can be used. This consists in super-imposing to the live view (for example, fluoroscopy without contrast agent) an anatomic representation of the anatomy (for example, contours of the aortic root as extracted from a reference aortagram, an anatomy model derived from 3D pre-interventional data, or combination of both, or any other suitable representation). This anatomy representation can be then be correctly registered with the live images. The continuous registration process with live images is often referred to as tracking.

For example, one can resort to the presence of a device located in correspondence with an anatomy referential, for example a device already present because required for other operational reasons, and can use information about the device as a mediator for the registration of the anatomy representation with the 2D live data. This has the advantage that it allows anatomy-to live image registration without resorting to calcifications which are in general very faintly contrasted, and the good visualisation of which is not entirely guaranteed.

Exemplary embodiments of the invention will be described in the following with reference to the following drawings.

Figure 1:
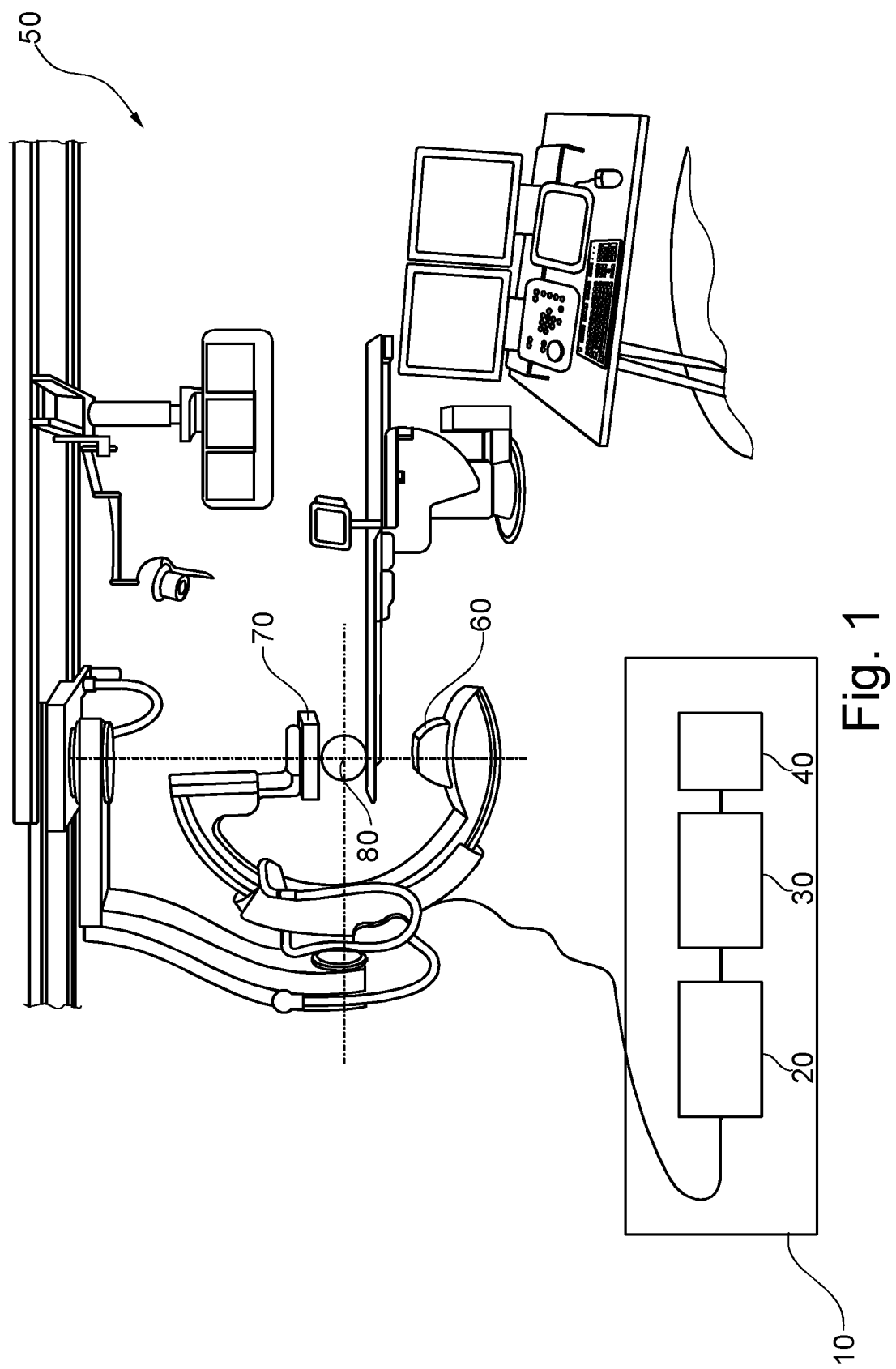
FIG. 1 illustrates an X-ray imaging system according to an exemplary embodiment of the invention.

FIG. 1 illustrates an X-ray imaging system 50 containing an apparatus 10 for pairing an anatomy representation with live images. Although FIG. 1 is showing the apparatus 10 in the context of an X-ray imaging system 50, the apparatus 10 can be a stand-alone apparatus and can be provided separately. The X-ray imaging system 50, although shown in FIG. 1 with reference to a C-arm system, can be any other X-ray system.

The X-ray imaging system 50 may comprise an X-ray source 60 and an X-ray detector 70. The X-ray source 60 is configured to radiate X-ray radiation towards the detector 70 radiating at least a part of a region of interest of an object 80. The X-ray detector 70 is configured to provide the reference projected-anatomy image data of the device, and to provide the at least one live image.

Before further describing the X-ray imaging system 50 and the apparatus 10, examples of a method for pairing an anatomy representation with live images reference structure are described in further detail with reference to FIG. 3.

Figure 3:
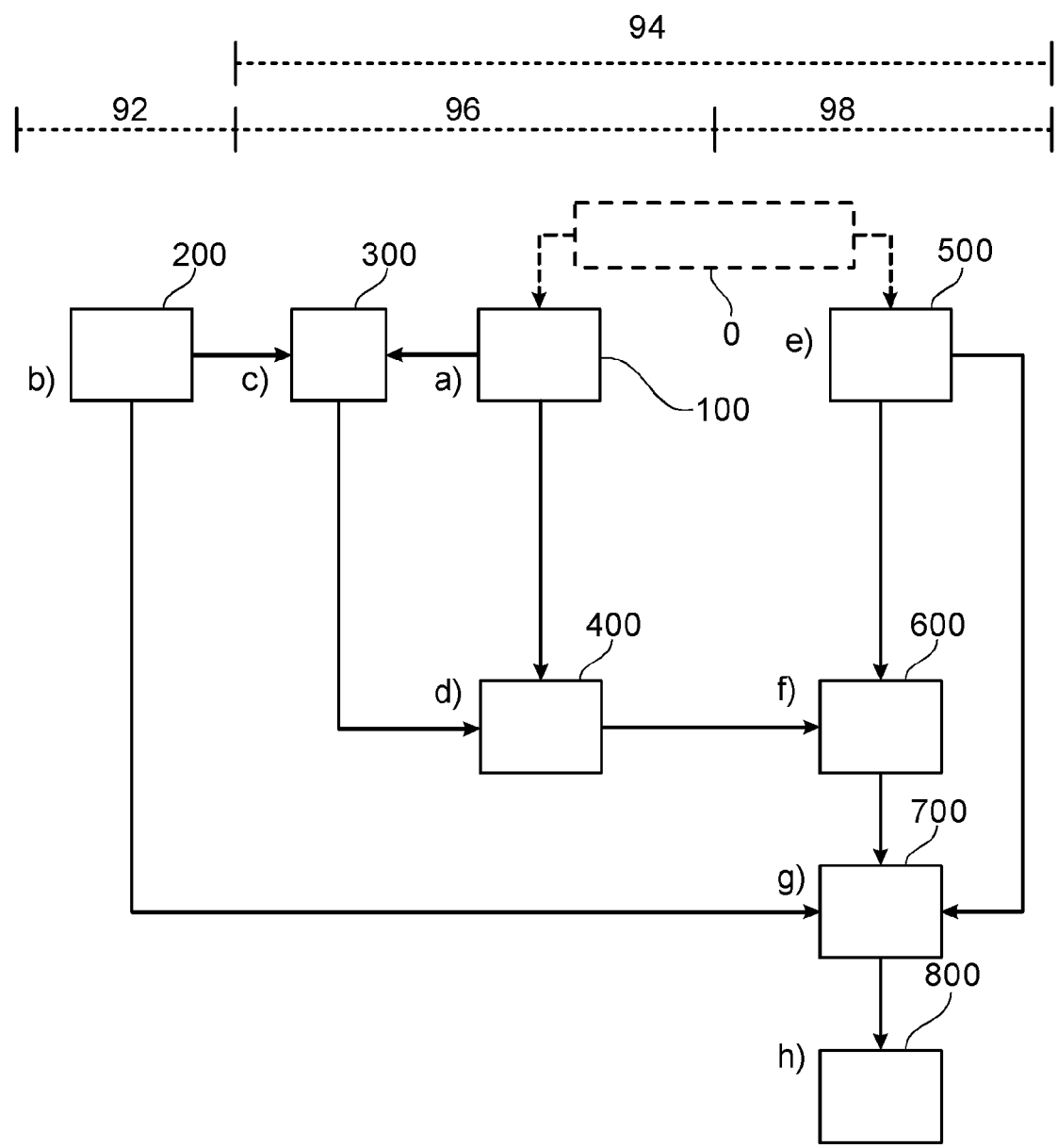
FIG. 3 schematically shows basic steps of a method for pairing an anatomy representation with live images according to an exemplary embodiment of the present invention.

In FIG. 3, a method for pairing an anatomy representation with live images is described, comprising:

In a first step 100, reference projected-anatomy image data of a device in a spatial relation to the anatomy is provided, the image data comprising at least a first and second image showing the device from different viewing angles.

For example, reference projected-image data can be a pair of aortagrams as routinely performed in operational interventions in order to assess the situation.

In a second step 200, an anatomy representation with an anatomy frame of reference is provided.

For example, an anatomy representation can describe a valve and its surroundings. The anatomy representation can be derived from a pre-interventional 3D data-set, for example from a CT scan or according to any other known technique. The anatomy representation can, for example, contain a 3D representation of the aortic root, of the various valve elements, of the possible calcification spots surrounding the valve or it can contain other alternative or additional details. Moreover, the representation can also combine elements from pre-interventional and peri-interventional sources.

In a third step 300, the anatomy representation is brought into spatial coherence with the at least first and second image of the reference projected anatomy image data.

For example, in case the reference projected anatomy image data are aortagrams, this step can include performing a co-registration of the anatomy representation with the aortagrams. For example, the anatomy representation can be brought into spatial coherence simultaneously with several reference projected anatomy images or aortagrams. For example, this can be done by finding several spatial transforms Ts (A→R), s for plural, which will make a projected anatomy A correspond with a 3D anatomy representation R. In this co-registration task, the device can be minimally involved, since it is not necessarily present in the 3D anatomy representation. For example, the footprint of the contrast agent in the 2D projection images can be used, in addition or in alternative to other references.

In a fourth step 400, a three-dimensional model of the device within the anatomy frame of reference is computed from the projected anatomy image data.

For instance, the model can be constituted of the 3D centreline and, for each point of this centreline, of an elliptical or parametric cross-section around that point. Such a model constitutes a good description of a tube-like device such as a catheter. Computing such a centreline amounts to define a certain number of corresponding points in the two or more projected anatomy images, to locate those points in 3D space (which is possible since represented by several projections under different angulations), to link those 3D points by a 3D curve that correctly fits the device footprint in every projection. The corresponding points must be chosen unambiguously. These are for instance points of locally maximal curvature. Computing, for every centreline point, an elliptic or parametric cross-section can be achieved in finding the device width in each projection image at the location of the centreline point, and to match the ellipse or parametric cross-section to those found widths.

In a fifth step 500, at least one live image containing the device is provided.

For example, a 2D live image can be acquired. Further, the 2D live image can be acquired under any viewing angle. The live image should contain the device in a spatial relation to the anatomy.

In a sixth step 600, the model and the at least one live image are registered based on the device information contained in the live image.

In a seventh step 700, the anatomy representation is brought into spatial correspondence with the at least one live image based on the registering of the model and the at least one live image.

For example, after the application of the T (R→L) transform, the anatomy representation is brought into spatial correspondence with the live images.

In an eighth step 800, the registered anatomy is combined with the at least one live image.

For example, this can include merging both data streams. The result of this combination can be, for example, a sequence of live images on which the registered anatomy representation is overlaid one way or the other. For instance, the outline of a valve as projected onto the image plane can be visualized. In addition to the pure anatomy information, this representation might include geometrical elements such a schematic representation of the valve plane (for example seen in projection as a line or a parallelogram, or any other suitable form of representation), which can be useful in the context of valve fine positioning.

The first step 100 is also referred to as step a), the second step 200 as step b), the third step 300 as step c), the fourth step 400 as step d), the fifth step 500 as step e), the sixth step 600 as step f) the seventh step 700 as step g), and the eighth step 800 as step h). For the order of the steps, see above.

A further aspect is also indicated in FIG. 3 with dotted lines. For example, the method relates to data from three different phases. A first phase 92 may be a pre-procedural or pre-operational phase in which the anatomy representation is prepared, for example by computing and processing previously acquired image data. A second phase 94 may be an intra-procedural or intra-operational phase. This second phase can be divided into a first sub-phase 96, in which the reference projected-anatomy images are acquired, and a second sub-phase 98, in which the live images are acquired. For example, the first sub-phase 96 is a contrast agent injected phase, and the second sub-phase 98 is a current phase without contrast agent. It is noted that these features, although shown in FIG. 3, are provided as additional features. Thus, they are provided as an option for the basic features described further above.

Figure 4:
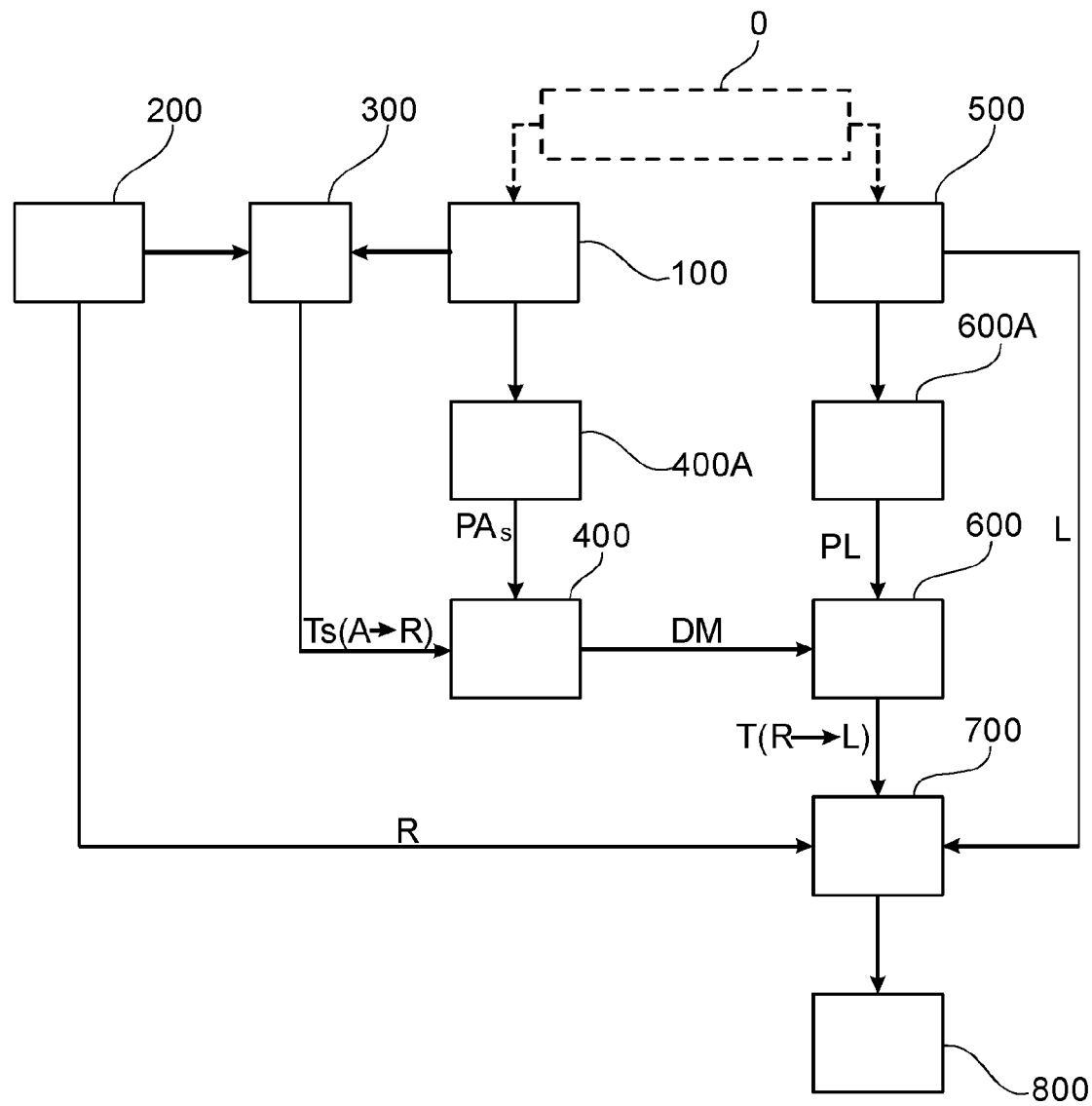
FIG. 4 shows a further example of a method according to the present invention.

As shown in FIG. 4, the computing step 400 can, for example, include additional steps such as device processing 400A in the input aortagram. For example, the information of the device from the reference-projected anatomy images can be processed in order to produce material for the subsequent modeling 400. For example, techniques such as hard segmentation (device's footprint identification) or to filtering (ridgeness, direction) can be used in addition or in alternative to other techniques. The resulting material is represented by Processed Angiograms, s for plural, referred to as PAs. For example, the 3D device modeling within the anatomy in step 400 can use information such as the above described spatial transforms Ts (A→R) and the above described device material PAs to produce a 3D model of the device, in short DM, within the anatomy. The anatomy representation of step 200 is also referred to as R, and the live images of step 500 as L. The reference projected-anatomy image is referred to as A.

For example, this can include the following approach:
First, aligning each projected-anatomy image with the 3D anatomy representation, for example through the separate application to each Ts (A→R) transform.
Then, the 3D modeling can be realized.
For example, realizing the 3D models can include using one or more of:
The back projections in space of the device centrelines as seen in the projections.
The computing of a 3D line at the intersection of surfaces produced by those back-projections.
The fitting of 3D parametric sections matching the device footprints in the projections.

As also shown in FIG. 4, the registration step 600 can, for example, include additional steps such as device processing 600A in the live images. For example, the information of the device from live images can be processed in order to produce material for the subsequent registration 600. For example, for such device processing 600A, techniques such as hard segmentation (device's footprint identification) or to filtering (ridgeness, direction) can be used in addition or in alternative to other techniques. The resulting material is represented by Processed Live image, referred to as PL.

Registering the model and the at least one live image 600 can include a device-based 2D-3D registration. For example, relying on the device originated material, the device model DM, which was computed within the anatomy referential, is brought into correspondence with the device footprint PL of the live image. As a consequence, the 2D-3D registration benefits from a starting research point around the projection of the device model onto the chosen live plane, known from the live acquisition parameters. The registration step 600 can include producing a T (R→L) transform linking the device in the live images with the device model, and consequently with the anatomy representation.

It is noted that the above-described examples relate to techniques for image pairing using advantageously the information about a device already being in a spatial relation to the anatomy. The device is normally already present for other reasons, related to the interventional context. Although not forming part of the method itself, this fact is shown schematically in FIG. 3 by the dashed block 0.

For example, the spatial relation can be achieved by a locking of the device in the anatomy, i.e. a state where movement of the device is at least very minimal with respect to the considered anatomy part, if not suppressed completely.

For example, an enforcement protocol is provided. This so-to-speak entry of the method steps symbolically represents one aspect of the invention that consists in enforcing both at aortagram and live times the locking of device (typically a pigtail catheter or any intervention-relevant radio-opaque device) in a location that is spatially tightly connected to the target anatomy (e.g. the valve and aortic root). A valve sinus (FIG. 2) is typically an anatomic location where such a locking is readily achieved. In practice, this spot is already used for the "parking" of the pig-tail (FIG. 3). The device can stay in place, up to the valve final deployment, where it should be removed if one does not want to face device jailing. But this means that the device can stay put during the full fine placement phase.

With reference to the above-described method, when obtaining the aortagram and the live images, the reference device can be any intervention-relevant radio opaque device placed in a location which is spatially tightly connected to the target anatomy, for example the valve and aortic root.

Figure 2:
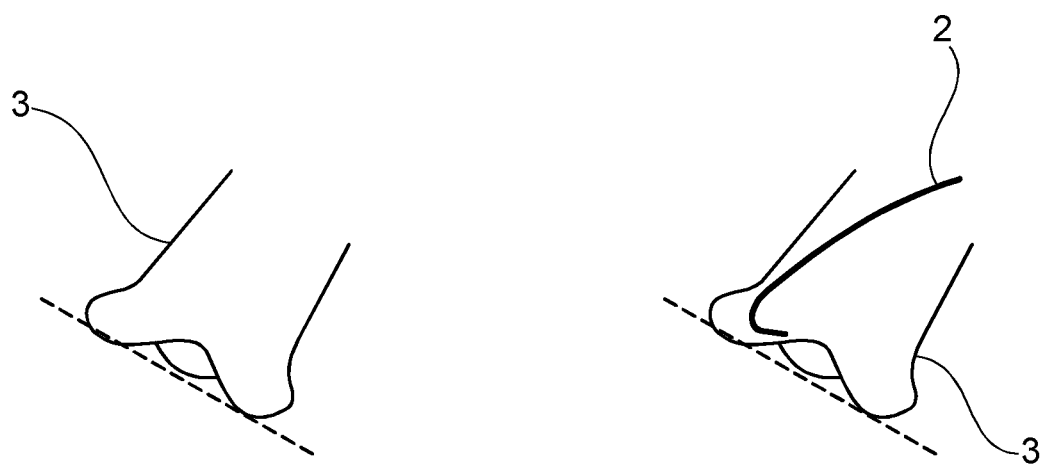
FIG. 2 illustrates an example of a device in a spatial relation to an anatomy according to an exemplary embodiment of the present invention.

For example, the device can be a pig-tail catheter 2 as shown in FIG. 2, such as when the present method is used in the context of TAVI. The pig-tail catheter 2 can be fixed in one of the valve sinus, as exemplarily shown in FIG. 2. A valve sinus is typically an anatomic location where such stable positioning of the device can readily be achieved, as this spot is normally used for the parking of the pig-tail. Such a device can stay in place up to the valve final deployment and it can be removed afterwards, to avoid any jailing. This means that such a device can, for example, remain in the same location during the full time of the valve placement phase. Moreover, although in the previous description the word "device" has been used, whenever the word "device" is mentioned it is understood that this might indeed refer to a full device but also to just a fraction of a device. For example, only the tip of an injection catheter can be suitably placed in relation to the anatomy. Moreover, the device can also be a device that moves independently from the anatomy. In this case, only the part of the device that moves in coherence with the anatomy can be considered for the above described device modeling, device processing, device based registration and any other step that might involve only a part of the device.

Although FIG. 2 is showing an example of a catheter in an aortic root sinus, the device can be any other device, and the anatomy referential can be any other anatomy referential suitable for the establishment of a spatial relation with a device Of course, what is described in the context of TAVI can be used in other interventional X-ray contexts, such as intra-cardiac applications in general (i.e. PFO closure of AF interventions) or in interventional oncology or, for example, in any intervention where a 3D anatomy representation is to be registered with X-ray images. The described method can be applied in X-ray Cathlab systems, for example in an Operating Room environment. It can also be applied in other situations such as EP or structural-heart-disease, or vascular interventions.

However, it is noted that, although the above examples relate to a possible use in the context of interventional X-ray, the described method is merely concerned with the information acquisition and processing used for the pairing of an anatomy representation with live images. Thus, the steps of the method itself do not require any manipulation of the device within the anatomy and the described imaging method indeed does not require any surgical step in itself for being carried out. The fact that the method can be used, in a potentially advantageous way, also in the course of a surgical intervention, does not preclude the described imaging method from being used, per se, in a variety of other different contexts where a similar image processing could be of advantage.

According to a further example, the at least one live image has any viewing angle. This provides the advantage of coping with any live viewing angle changes without resorting to new specific acquisitions of a contrast-injected angiogram, which would require an additional X-ray dose, additional contrast agent and a disrupted workflow. For example, the viewing angle of the at least one live image is different from the viewing angle of the least first and second image of the reference projected image data.

The above described device-based anatomy representation-to-live-data registration process is, thus, capable of coping with live viewing-angle changes without resorting to new specific acquisitions, and without workflow disruption.

For example, the reference projected-anatomy image data are obtained using a contrast agent and the at least one live image is obtained without use of a contrast agent.

The above described method is used, for example, for assistance during Trans-catheter Aortic Valve Implantation (TAVI).

In further examples of the method, the temporal aspect is introduced, for example when acquiring the reference projected-anatomy images and the live images based on the principle that what the invention achieves on one live image, can also be achieved on a succession of live images.

Figure 5:
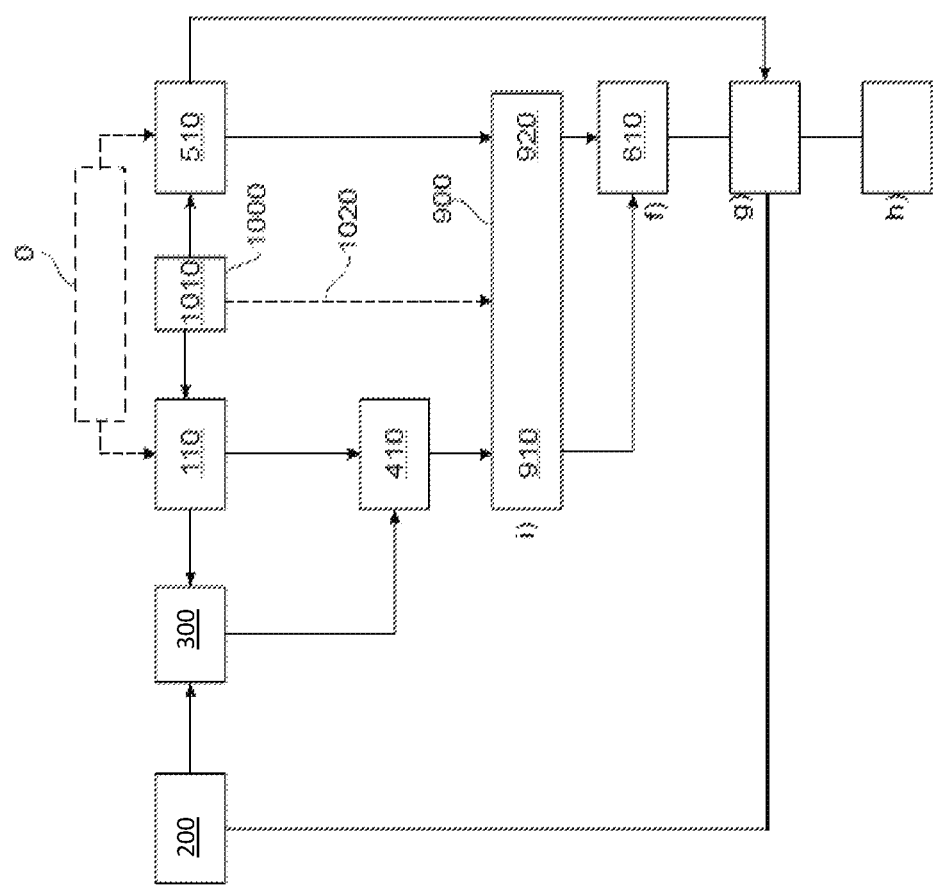
FIG. 5 shows a further example of a method according to the present invention.

According to a further example, shown in FIG. 5, the anatomy is subjected to a (natural) regular motion within its frame of reference, which motion can be decomposed in several repetitive motion phases. In a second step 200, an anatomy representation with an anatomy frame of reference is provided. In a third step 300, the anatomy representation is brought into a spatial coherence with the at least first and second image of the reference projected anatomy image data. The method may further comprise the following: In step a), the reference projected image data are a sequence 110 of reference projected image data along time, containing the anatomy during its several motion phases. In step d), a sequence 410 of three-dimensional models of the device along time is computed. In step e), a sequence 510 of live images along time is provided. The method further comprises the step: i) Selecting 900 at least one three-dimensional model along time and at least one live image along time, corresponding to the same motion phase. In step f), a registration 610 is performed between the at least one selected three-dimensional model and at least one live image corresponding to a same motion phase. The selection step 900 is indicated with a common frame for a first selecting sub-step 910 of selecting the respective three-dimensional model along time, and a second selecting sub-step 920 of selecting the respective at least one live image along time.

For example, the motion phases are cardiac phases.

For example, in a timing or gating step 1000, a time or gating signal 1010 is provided to the reference projected-anatomy image sequence 110 and the sequence 510 of live images along time. A dashed arrow 1020 indicates that the selecting sub-steps refer to the same time or gating signal. The gating signal may relate to cardiac phases.

For example, if the anatomy is subjected to a periodic motion, such as heart beating, then instead of creating only one 3D device model, one might create a 4D device model. A 4D device model can, for example, be created using several 3D models along time, through the use of two full projected-anatomy sequences covering a corresponding period.

The period can, for example, be a cardiac cycle.

For example, a 4D device model can be created based on the appropriate pairing of the projected-anatomy images acquired. A registration of the anatomy with the live images can be obtained through the appropriate pairing of the live images with the correct 3D model. For example, an appropriate pairing can be obtained, as described above, based on a time-correspondence.

For example the time-correspondence can be represented by having the same cardiac phase. The cardiac phase can be determined, for example, according to one or more technique, such as ECG gating or any other known technique.

For example, a rotational scan with contrast agent injection can be used to produce the 3D/4D anatomy representation during the intervention (peri-interventional) while the device remains in the same spatial relation to the anatomy during the full scan. In this case, the 3D or 4D device model to be used according to the method described above can, in the alternative, be directly deduced from such an anatomy representation without resorting to the several extra projected anatomy images.

The anatomy representation might be 3D+time, for instance, CT cardiac scan producing several volumes corresponding to several cardiac phases, for example ten phases. What has been described referring to the pairing of the angiograms and the live images (step 900) is also provided for the pairing of the right anatomy representation with the right angiograms. Thus, step 900 may also address the anatomy representation. For example, the anatomy representation is paired to the angiograms, and the angiograms are paired to the live images.

It is noted that the features of the method shown in FIG. 3 can of course be combined with both examples shown in FIG. 4 and FIG. 5.

As indicated above, FIG. 1 illustrates the apparatus 10 according to the present invention. The apparatus 10 for pairing an anatomy representation with live images comprises an interface unit 20 and a processing unit 30. The interface unit 20 is configured to provide reference projected-anatomy image data of a device in a spatial relation to an anatomy. The image data comprises at least a first and second image showing the device from different viewing angles. The interface unit 20 is further configured to provide at least one live image containing the device. The processing unit 30 is configured to provide a representation of the anatomy with an anatomy frame of reference, and to bring the anatomy representation into spatial coherence with the at least first and second image of the reference projected anatomy image data. The processing unit 30 is also configured to compute a three-dimensional model of the device within the anatomy frame of reference from the projected anatomy image data, and to register the model and the at least one live image based on the device information contained in the live image. The processing unit 30 is further configured to bring the anatomy representation into spatial correspondence with the at least one live image based on the registering of the model and the at least one live image, and to combine the registered anatomy with the at least one live image.

According to a further example, the apparatus 10 comprises a display unit 40 configured to visualize a live image overlaid, or otherwise combined, with the anatomy representation.

According to a second aspect of the present invention, the X-ray imaging system 50 is provided, comprising the apparatus 10 described above.

It is understood that, without repeating here all the examples and explanations provided with reference to the method of the invention, the apparatus 10 and system 50 of the invention are intended as being arranged to carry out the above described method. Thus, all of the above examples and explanations, although firstly provided with reference to the method, are also to be intended as being implemented by the apparatus 10 and X-ray system 50. This can be achieved, for example, by means of suitable hardware and/or software.

Thus, according to a further example of the present invention, a computer program element is provided, which, when being executed by a processing unit is adapted to carry out the method described above.

According to further example of the present invention, a computer readable medium having stored thereon a program element is provided, which, when being executed by a processing unit is adapted to carry out the method described above.

According to a further example of the present invention (not shown), a method for operating a device is provided comprising the following steps: a) pairing an anatomy representation with live images according to the method described above and b) visualizing a live image overlaid with the anatomy representation.

The computer program element might be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for pairing an anatomy representation with live images, comprising:

an interface unit; and a processing unit;

wherein the interface unit is configured to provide reference projected anatomy image data of a device in a spatial relation to an anatomy, wherein the image data comprises at least a first and second image showing the device from different viewing angles; and to provide at least one live image containing the device;

wherein the processing unit is configured to provide the anatomy representation with an anatomy frame of reference; to bring the anatomy representation into spatial coherence with the at least first and second image of the reference projected anatomy image data; to compute a three-dimensional model of the device within the anatomy frame of reference from the reference projected anatomy image data of the device; to register the model and the at least one live image based on device information contained in the live image; to bring the anatomy representation into spatial correspondence with the at least one live image based on the registering of the model and the at least one live image; and to combine the registered anatomy representation with the at least one live image.

2. The apparatus according to claim 1, further comprising a display unit, wherein the display unit is configured to visualize a live image overlaid with the anatomy representation.

3. An X-ray imaging system (50), comprising:
   an X-ray source;
   an X-ray detector; and
   the apparatus according to claim 1;
   wherein the X-ray source is configured to radiate X-ray radiation towards the detector radiating at least a part of a region of interest of an object;
   wherein the X-ray detector is configured to provide the reference projected-anatomy image data of the device; and to provide the at least one live image.

4. A method for operating the X-ray imaging system of claim 3, wherein the X-ray imaging system further comprises a display unit, and wherein the interface unit is further configured to pair the registered anatomy with at least one live image by overlaying the anatomy representation with the at least one line image, the method of operating the X-ray imaging system comprising:
   visualizing a live image overlaid with the anatomy representation.

5. A method for pairing an anatomy representation with live images, comprising the steps of:
   a) providing reference projected anatomy image data of a device in a spatial relation to an anatomy, wherein the image data comprises at least a first and second image showing the device from different viewing angles;
   b) providing the anatomy representation with an anatomy frame of reference;
   c) bringing the anatomy representation into spatial coherence with the at least first and second image of the reference projected anatomy image data;
   d) computing a three-dimensional model of the device within the anatomy frame of reference from the projected anatomy image data of the device;
   e) providing at least one live image containing the device;
   f) registering the model and the at least one live image based on device information contained in the live image;
   g) bringing the anatomy representation into spatial correspondence with the at least one live image based on the registering of the model and the at least one live image; and
   h) combining the registered anatomy representation with the at least one live image.

6. The method according to claim 5, wherein the at least one live image has any viewing angle.

7. The method according to claim 5, wherein the reference projected-anatomy image data are obtained using a contrast agent, and the at least one live image is obtained without use of a contrast agent.

8. The method according to claim 5, wherein the method is used for assistance during Trans-catheter Aortic Valve Implantation (TAVI).

9. The method according to claim 5, wherein said device is a pig-tail catheter or a part thereof.

10. The method according to claim 5, wherein:
    the anatomy is subjected to a (natural) regular motion within its frame of reference, which motion can be decomposed in several repetitive motion phases; in step a), the reference projected image data is a sequence of reference projected image data along time, containing the anatomy during its several motion phases;
    in step d), a sequence three-dimensional models of the device is computed along time;
    in step e), a sequence of live images along time is provided;
    wherein the method further comprises a further step i) of selecting (910) at least one three-dimensional model along time and selecting at least one live image along time corresponding to a same motion phase; and
    wherein in step f), a registration is performed between the at least one selected three-dimensional model and at least one live image corresponding to the same motion phase.

11. A tangible non-transitory computer readable storage medium that stores a computer program, the computer program, when executed by a processor, causes the processor to perform the method according to claim 5.

* * * * *